United States Patent [19]

Numa et al.

[11] Patent Number: 5,726,062
[45] Date of Patent: Mar. 10, 1998

[54] METHOD OF DETECTING PROTEIN AND A KIT DETECTING PROTEIN USING THE SAME

[75] Inventors: Masayuki Numa; Masahiko Yamazaki, both of Tokyo, Japan

[73] Assignee: Konica Corporation, Tokyo, Japan

[21] Appl. No.: 633,043

[22] Filed: Apr. 16, 1996

[30] Foreign Application Priority Data

Apr. 19, 1995 [JP] Japan .................................. 7-093690

[51] Int. Cl.$^6$ ........................................... G01N 33/68
[52] U.S. Cl. ................................... 436/86; 422/58; 422/61
[58] Field of Search ............................. 422/56, 58, 61; 436/86

[56] References Cited

U.S. PATENT DOCUMENTS

| | | |
|---|---|---|
| 3,936,271 | 2/1976 | Statter . |
| 5,256,537 | 10/1993 | Phillip et al. ............ 422/61 |
| 5,425,915 | 6/1995 | Phillip et al. ............ 422/61 |
| 5,550,061 | 8/1996 | Stone .................... 422/56 |

FOREIGN PATENT DOCUMENTS 08021837A 1/1996 Japan .

OTHER PUBLICATIONS

Pierce Immuno Technology Catalog & Handbook, pp. 44–45, no date supplied.

*Primary Examiner*—Lyle A. Alexander
*Attorney, Agent, or Firm*—Finnegan, Henderson, Farabow, Garrett & Dunner, L.L.P.

[57] ABSTRACT

A method for detecting protein present on the surface of a sample and a kit for performing protein detection applying the detecting method are disclosed. The method is comprising the steps of (1) transferring substances present on the subject portion of the surface of a sample to a sampling means which comprises a water absorbable portion comprising a water-insluble sythetic polymer, (2) contacting the substances transferred to said sampling means with a reagent capable of forming color upon reaction with protein, and (3) measuring color formed by the reaction of said reagent with protein to determine the amount of protein contained in the substance transferred to the sapling means. The kit includes the sampling means and the color forming reagent in combination.

9 Claims, 6 Drawing Sheets

METHOD OF DETECTING PROTEIN AND A KIT DETECTING PROTEIN USING THE SAME

FIELD OF THE INVENTION

The present invention relates to a method of detecting protein and a kit for detecting protein using this method.

BACKGROUND OF THE INVENTION

So that disasters derived from eating and drinking may not take place for the public health, it is necessary for quality and condition of additives, containers, packages, the environment concerning food and drink to be controlled adequately. Accordingly, a method for easily detecting protein present on the surface of an object relating to foodstuffs is strongly demanded.

The methods of detection of protein heretofore known in the art necessarily stick a reagent directly to a sample or a subject material, there have been problems of contamination of the subject sample and safety of the residual reagents. Also, there has been a problem that colored materials formed from the reagent remain on the sample and they can hardly be removed with water. Further, there has been a problem that according to the above-mentioned detection method, it is rather difficult carry out quantitative measurement, and, in addition, there has been a case where 3 to 72 hours or more were necessary to obtain a result.

Japanese Patent Publication Open for Public Inspection (JP O.P.I.) No. 8-021837 discloses a technology to detect the presence of protein by transferring substances to be detected from the surface of a sample to a sampling means, by which the problem of contamination of the sample was solved, danger due to the residual reagent can be minimized, quantitative analysis can be performed, colored material of the reagent seldom remains on the sample, and detection time can be expedited. In this technology, the water absorbable portion of the sampling means is mainly made of natural cellulose such as cotton fibers. The fiber is intertwined to raise water absorption property thereof and formed in such a form of a cotton stick in the practical use. In the case using such sampling means, there have been problems that range of measurement is narrow and reproducibility is poor since background noise of the measurement is high. The background noise is caused by color formation by the sampling means itself without any sampled substance. Hereinafter, the background noise is referred to "background coloring".

SUMMARY OF THE INVENTION

The object of the present invention is to provide a method of detecting protein and a kit for applying the method with enhanced reproducibility and lowered background noise or background coloring of the measurement.

The above-mentioned object of the invention can be attained by a method for detecting protein present on the surface of a sample comprising the steps of (1) transferring substances present on the subject portion of the surface of a sample to a sampling means which has a water absorbable portion comprising a water-insoluble synthetic polymer, (2) contacting the substances transferred on the sampling means with a reagent capable of forming color upon reaction with protein, and (3) measuring color formed by the reaction of said reagent with protein to determine the amount of protein contained in the substance transferred on the sampling means.

The kit for detecting protein using the above method of the invention is a combination of tools including the above-mentioned sampling means comprising a water-insoluble synthetic polymer for transferring the substances from the surface of the sample and a reagent capable of reacting with a protein and forming a color.

DETAILED DESCRIPTION OF THE INVENTION

Figure 1A:
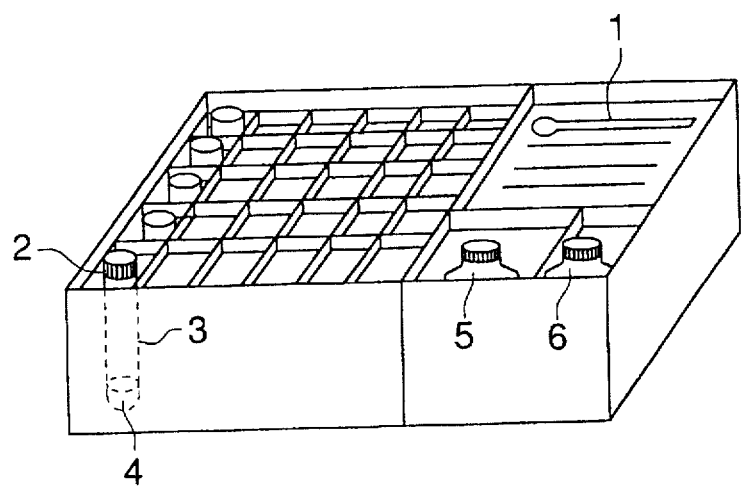
FIGS. 1a to 1c are structural drawings of protein detection Kit A, which is one of the preferable embodiments of the present invention.

The method of the invention is a method for quantitatively detecting protein during a shorten period of 1 to 60 minutes, which is carried out by the following procedure. Protein to be detected is transferred from the subjective portion of the surface to a sampling means. The sampling means on which the substances are transferred from the sample surface is contacted with a previously prepared solution of a reagent capable of forming color by reaction with protein. Then the qualitative detection of protein is carried out by measuring the optical density of color formed by the reaction by a spectral densitometer of a color meter and a calibration curve, i.e., a curve showing the relation of between the amount of protein and color density, or by comparison with a color standard samples showing color density corresponding to the amount of protein contained in the substance transferred from the sample surface.

The term of "sample" used in the present invention, means a subject, as to which detection of protein on the surface of it is to be investigated.

In the invention, the sampling means comprises a water-insoluble synthetic polymer to which protein present on the surface of the sample can be transferred. As for such synthetic polymers, for example, the following materials may be mentioned:

Nylon-type polymer: a polymer having a polymerizing unit of —(NH(CH$_2$)$_x$NH—CO(CH$_2$)$_y$—CO)—, in which x and y are each an integer representing the number of the methylene group;

Polyester-type polymer: a condensation polymer of a polyol and a polybasic acid having a —CO—O— bonding;

Acryl polymer: a polymer of acrylonitrile CH$_2$=CHCN;

Polyvinyl alcohol-type polymer: a polymer having a polymerizing unit of —(CH$_2$C(OH)H)—;

Polyurethane-type polymer: a polymer having so-called a urethane bond, —(NHCOO)—;

Polyvinylidene chloride-type polymer: a radical polymerized polymer of vinylidene chloride having a polymerizing unit of —(CH$_2$CHCl$_2$)—;

Polyvinyl chloride-type polymer: a polymer of vinyl chloride having a polymerization unit of —(CH$_2$CHCl)—;

Polyfluoroethylene-type polymer: a polymer of fluoroethylene

Polypropylene-type polymer: a polymer of propylene having a polymerizing unit of —(CH$_2$(CH$_3$)CH$_2$)—; and Polyethylene-Type polymer: a polymer having a polymerizing unit of —(CH$_2$CH$_2$)—; and a copolymer of the above-mentioned polymerization units.

Among these polymers, preferable ones are polymers of polyester-type, polyvinyl alcohol-type, polyvinylidene chloride-type, poll/vinyl chloride-type, polypropylene-type, and polyethylene-type. Especially preferable polymers in the light of low background coloring level and reproducibility are polymers of polyester-type, polypropylene-type and polyethylene-type.

The form of the water-insoluble synthetic polymer as the material for comprising the water absorbable portion of the sampling means may be of any form so far as it has a portion having a high water absorbness and water-holding properties. It is preferred, for example, that the water-absorbable portion is comprised of fibers of the sythetic polymer which are put together to form a swab or a swab fixed on a stick, or a membrane of the sythetic polymer having a high porasity or many slits. The preferred form of the water-insoluble synthetic polymers includes forms of fiber, cloth, sponge and filter paper. The water-insoluble synthetic polymer may be singly used as a sampling means. In such case, a piece of the polymer, for example, in the above-mentioned form, is held by a holding means such as a pair of tweezers for contacting to a sample surface. Moreover, it is preferable for convenience of sampling to attach a holding member with the water absorbable portion comprised of the water-insoluble synthetic polymer. Examples of such sampling means include the followings.

A swab-stick-shaped sampling means which composed of a water absorbable portion comprised of the polymer attached at an end of a stick.

A tape-shaped sampling means which is composed of a water absorbable portion comprised of the polymer provided on a tape-shaped holding member.

A stamp-shaped sampling means in which a water absorbable layer comprised of the polymer is attached on a stamping surface of a stamp-like handle.

A filter paper-shaped sampling means which is comprised of the fiber of the polymer made in a form of a filter paper.

A strip-shaped sampling means which composed of a substrate such as a plastic film and a water absorbable layer comprised of the polymer provided on the substrate remaining a space for handling and cut in a form of a strip.

Concerning the method of transferring substances onto the above-mentioned sampling means, for example, by means of wiping, pressure contacting and absorbing can be mentioned. For the method of wiping, for example, a method of using a swab in a shape of cotton pad or a membrane filter can be mentioned. For the method of pressure contacting, for example, pressure contacting with a tape, stamp or a stripping substratum or a method of pressure contacting a roller with a sticking material can be mentioned. Further for the method of absorbing, for example, a method of directly absorbing using the swab-stick-shaped or the filter paper-shaped sampling means can be mentioned.

In the case of the absorbing method, for example, such a method, in which a solution containing a surface active agent is dropped on the surface of a sample and stood for a moment to soak up the substances present on the surface, is preferable for enhancing the effect of the present invention. In such the case, the solution after standing may be sucked up by a pipette and transferred to the sampling means of the invention.

The sampling means used in the present invention preferably has a water absorbable portion wettable with an aqueous medium and, more preferably, the water absorbable portion is made wet in advance to use with an aqueous medium.

As the above-mentioned aqueous medium, for example, an isotonic sodium chloride solution, purified water such as distilled water or deionized water, an aqueous solution containing a surface active agent, an aqueous 2–95% solution of a water miscible organic solvent such as acetone, ethanol, propyl alcohol or methylethyl ketone can be mentioned.

For examples of the surface active agent usable in the above -mentioned aqueous solution containing a surface active agent, the following can be mentioned.

Nonionic surface active agents:

1. An aliphatic acid ester of sorbitan.
2. An aliphatic acid ester of glycerin.
3. An aliphatic acid ester of decaglycerin.
4. An aliphatic acid ester of polyglycerin.
5. An aliphatic acid ester of propylene glycol pentaerythritol
6. An aliphatic acid ester of polyoxyethylene sorbitan.
7. An aliphatic acid ester of polyoxyethylene glycerine
8. An aliphatic acid ester of polyethylene glycol.
9. An aliphatic ester of polyethylene glycol.
10. Polyoxyethylene alkylphenyl ether.
11. Polyoxyethylene phytosterol.phytostanol.
12. Polyoxyethylenepolyoxypropylene alkyl ether.
13. Polyoxyethylenealkylphenyl ether.
14. Polyoxyethylene caster oil-hardened caster oil.
15. Beeswax derivative of polyethylenelanoline and.lanoline alcohol.
16. Polyethylenealkylamine.aliphatic acid amide.
17. Polyethylenealkylphenyl-formaldehyde condensation product.
18. Single-chain polyoxyethylene alkyl ether.

The alkyl mentioned above include straight- or branched-alkyl group having one to 18 carbon atoms.

Anionic surface active agents;

1. Alkyl sulfates.
2. Polyoxyethylene alkyl ether sulfate.
3. N-acyl amino acid.
4. N-acyl taurinate.
5. polyoxyethylene alkylether acetate.
6. Alkylsulfonate, α-olefin carbonate, and
7. Alkyl phosphate, polyoxyethylenealkyl ether phosphate As the alkyl group mentioned above, one having one to eight carbon atoms are mentioned.

Cationic surface active agents:

1. Salts of alkylammonium.
2. Salts of alkylbenzylammonium

As the alkyl group mentioned above, one having one to eight carbon atoms are mentioned.

Amphoteric surface active agent:
1. Acetic acid betaine, imidazolium betaine
2. Lecithin As compounds which are available in the market, the following products can be mentioned.

Nonionic surface active agent: Triton X-100 sold by Wako Junyaku Kogyou Co., Ltd., Tween-20 sold by Wako Junyaku Kogyou Co., Ltd., Nonidet P-409 sold by Belinger-Manheim-Yamanouchi Co., Ltd.;

Anionic surface active agent: Triton X-770(sold by Sigma Cationic surface active agent: Benzalconium chloride;

Amphoteric surface active agent: AM-301(sold by Nikko Chemical Co., Ltd.)

The substances thus transferred to the sampling means from the sample surface are contacted with a reagent capable of forming color upon reaction with protein for detecting protein contained in the transferred substances. As the reagent for detecting the protein, those necessary for detection according to the various protein detecting method such as biuret reaction method, Lowry method, Coomassie dying method, BCA method and ninhydrin reaction method, are usable.

Although various methods can be optionally applied without any limitation for contacting the transfer substances and the reagent, a method in which the sampling means is directly immersed in the protein detecting reagent solution, and a method in which the substances are extracted from the sampling means into an aqueous medium and the reagent is added to the medium are preferably applied. In the later method of the above mentioned, the sampling means may be remained in the medium after addition of the detecting agent. Further a method in which the solution of the reagent is directly dropped on the sampling means on which the sampled substances are transferred is also preferably applied. As the aqueous medium for extraction of the substances from the sampling means, those foregoing as the aqueous media to be used for wetting the sampling means.

Although the reaction of the substances and the reagent can be performed under an ordinary temperature, it is preferred that the reaction is accelerated under a condition at 20° C. to 80° C., more preferably 30° C. to 60° C., for a time of 1 to 60 minutes. As the reagent capable of reacting with the above-mentioned protein and forming color, any one which is known in the art can be used, and these reagents may be used for the detection of the protein defined in the present invention by appropriately arranging one or more of reagents and preparing as a solution of protein detective coloring agent.

Upon preparation of the protein detective coloring agent, it is possible to add 0.1%–5% of sodium borate for the purposes of enhancing sensitivity of the protein detection and shortening of reaction time.

The protein detection kit for applying the above mentioned method of the invention include, for example, a sampling means according to the invention, a protein detecting reagent capable of reacting with protein and producing a color, a container for the reagent, a vessel in which reaction of the substances transferred to the sampling means with the reagent is conducted, such as a glass or plastic tube with a cap, a plate for titrating the protein reacting and color producing reagent, color samples, and a frame member by which rubbing area on the sample for transferring to the sampling means becomes constant are arranged as one set. More specifically, it is described in detail in the examples.

EXAMPLES

The present invention is explained more in detail with reference to examples below.

Example 1

1. Preparation of reagents

Preparation of protein-reactive coloring forming reagent R

Reagents A and B, of which compositions are given below, are prepared, and Reagent-A and Reagent B are mixed at the mixing ratio of 100:2 to prepare the protein-reactive color forming reagent R. Then optical density of colored solution at 562 nm is measured.

Preparation of Reagent-A

Deionized aqueous solution containing the following compounds is used as Reagent-A. Numerals are given in terms of weight %.

Disodium-2—2'-bicichoninate 1
$Na_2CO_3.H_2O$ 2
Sodium tartarate 0.16
NaOH 0.4
$NaHCO_3$ 0.95
Water 95.49

The value of pH of this solution is adjusted at 11.25 with 5% aqueous solution of sodium hydroxide or sodium hydrogen carbonate.

Preparation of Reagent-B

Deionized aqueous solution containing 4 weight % of cupric sulfate is used as Reagent-B.

The above-mentioned Reagents-A and Reagent-B are used in the kits, which are explained in detail below.

2. Figure of kit and measuring procedure

Below, figure and measuring steps according to the invention are explained.

At the time of handling the kit, one should be very careful not to directly touch the sample or the sampling medium with his finger or hand.

2-1 Protein detection Kit A

Figure 1B:
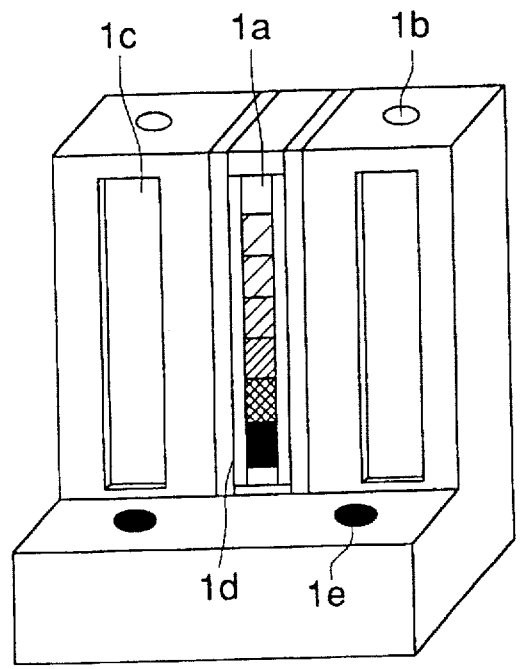
Figure 1C:
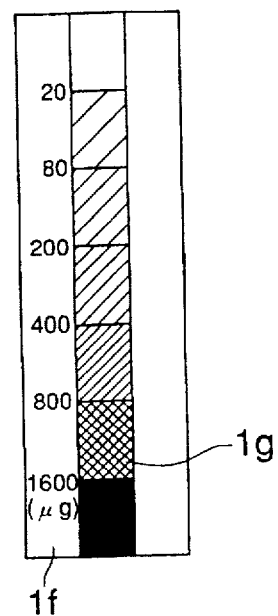

Structure of the protein detecting kit according to the present invention shown in FIGS. 1a to 1c is as follows. The kit comprises Reagent B contained in an eye-dropper-type bottle 5, an isotonic sodium chloride solution contained in an eye dropper-type bottle 6, a sampling swab 1 as a sampling means of the invention shaped like a swab-stick with a plastic stick of diameter of 2 mm and length of 75 mm and an end of which a swab composed of polyester fiber is attached, and a glass tube 3 having a diameter of 10 mm and a length of 70 mm with a cap 2, in which 1 ml of Reagent-A is contained.

Other than the above-mentioned, a thermostat which can be set at 60° C., a spectrophotometer by which optical density at 562 nm can be measured, a colorimeter, cf. FIG. 1b, a standard color scale, cf. FIG. 1c and a test tube stand are prepared.

In the case of the present kit, the colorimeter and standard color scale have been set in advance. In FIG. 1b and FIGS. 1c, 1a through 1g represent standard color scale, a light, a window for colorimetery, a holder for the standard color scale, test tube stand, quantity display for protein and degree of coloration, respectively.

Manner of operation of Kit A

Open the cap of the glass tube 3, add two drops of reagent-B and shake it to mix. Next, absorb a few drops, approximately 100 μl, of the isotonic sodium chloride solution into sampling swab 1, and wipe an area of 7 $cm^2$ of the sample without leaving any corner. At this time, as a criteria of strength of wiping, it may be to the extent that the stick of sampling swab 1 bends and about 20 strokes, by which the whole area of the subject portion can be wiped out. Then the sampling swab 1 is dipped into the glass tube 3.

On the other hand, another sampling swab not used is dipped into the other glass tube in the same manner for comparison. Warm the tubes at 60° C. for five minutes in the thermostat. Then cool the tubes to the room temperature, and compare color with that of the control using a colorimeter. The colorimeter is previously equipped with a standard color scale, and semi-quantitative measurement of the protein absorbed in the sampling swab 1 can be made by comparing with the standard scale.

Further, the quantity of the protein absorbed in the sapling Swab 1 can be determined more precisely by measuring optical density at 562 nm and by the use of a calibration curve, which is prepared in advance.

2—2 Protein detection Kit B

Figure 2:
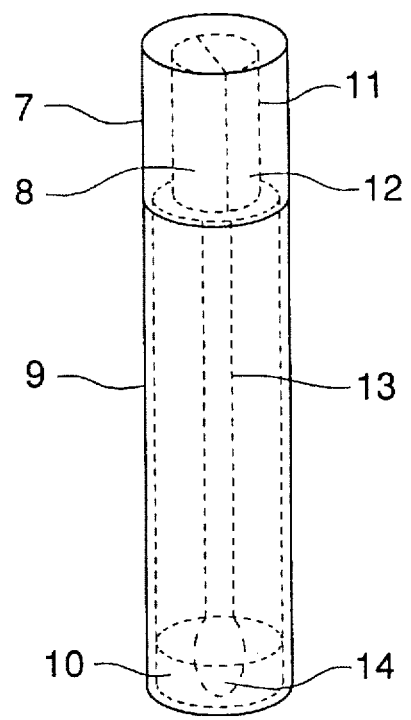
FIG. 2 is structural drawing of protein detection Kit B including a swab-stick-shaped sampling means, which is another preferable embodiment of the present invention.

Structure of a kit for detecting protein, which is another embodiment of the present invention, cf. FIG. 2:

Kit B contains a glass tube 9 having a diameter of 10 mm and a length of 75 mm length in which 500 µl of an aqueous sodium chloride solution 10 is contained. A cap 7 is attached to the tube 9, and flexible cases 11 which is divided two portions 8 and 12 each respectively enclosing Reagents A and B, is attached at the lower portion of the cap and a sampling swab 13 is fixed to the bottom of the cap 7. By clasping both ends of the cap 7, the flexible case 11 is destroyed, and Reagents A and B fall into the glass tube 9, and there, the reagents are brought into contact with the sampling swab 13 as a sampling means of the invention. Numeral symbol 14 stands for a detecting portion.

Other than the above-mentioned, a thermostatic bath which can be adjusted at 60° C. with a heater such as block-heater, a spectroscopic photometer by which optical density at 562 nm can be measured, a colorimeter, a standard color scale, if necessary, and a test tube stand are prepared.

Manner of handling of Kit B

Take off the cap 7, and transfer protein onto the sampling swab 13 from the sample in the similar manner in the operational manner of the above-mentioned Kit A,. Then bring the sampling swab 13 back to the glass tube 9 and close the cap 7. Next, destroy the flexible case 11, and drop Reagents A and B into the glass tube 9. After shaking the glass tube lightly to mix Reagents A and B, warm the glass tube to 60° C. for five minutes in the thermostatic bath. Then cool the tube down to the room temperature, and compare color formed in the solution in the tube with a standard color scale using a colorimeter. The standard color scale is previously prepared and equipped on the colorimeter. Thus the semi-quantitative measurement of the protein transferred on the sampling swab is performed.

Further, by measuring optical density at 562 nm, the quantity of the protein absorbed in the sampling Swab 13 can be made more precisely by the use of a calibration curve; which is prepared in advance.

2-3 Protein detection Kit C

Figure 3:
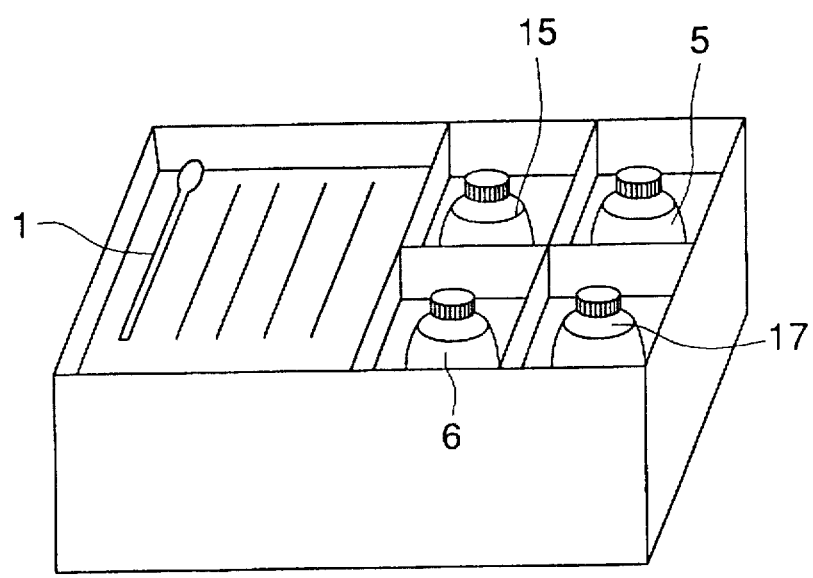
FIG. 3 is structural drawing of portable protein detection Kit C including a swab-stick-shaped sampling means, which is still another preferable embodiment of the present invention.

Structure of Kit C for detecting protein, which is still another embodiment of the present invention, cf. FIG. 3:

The kit is constituted by Reagent-A and reagent-B, which are each filled in bottles 15 and 5, respectively, having the shape of an eye drop bottle, an eye drop bottle-shaped bottle 17 for keeping Reagent R, an isotonic sodium chloride solution 6 filled in an eye drop bottle, a sampling swab 1 as a sampling means of the invention having the similar shape as the same used in the foregoing Kit A, and a glass tube with a diameter of 10 mm and a length of 70 mm.

Other than the above-mentioned, a thermostat which can be adjusted at 60° C. with a heater such as block-heater, a spectroscopic photometer by which optical density at 562 nm can be measured, a colorimeter, a standard color scale, if necessary, and a test tube stand are prepared.

Manner of handling Kit C

Put and lightly mix 1 ml of Reagent-A and a few drops of Reagent-B in the bottle 17 for the Reagent-R. The reagent-R thus prepared can be stably preserved for ten days under the normal temperature. Then, after making wet the head of the sampling swab 1 with few drops of the isotonic sodium chloride solution 6, transfer protein from the surface of a sample to the sampling swab 1 in the similar manner described in the operational manner of the above-mentioned Kit A Next, fall a few drops of the reagent-R on the head of the sampling swab 1. Immediately thereafter a coloring reaction initiates at the head of the swab, and. if necessary, stand it against an appropriate basis and leave it under the normal temperature or, if necessary, at 60° C. for one to 30 minutes in the glass tube. The head of the sampling swab 1 is colored from a faint green color to a reddish violet according to the amount of the protein adhered on the swab head. Semi-quantitative measurement of the protein transferred on the sampling swab 1 is performed by comparing color with the standard scale.

2-4 Protein detection Kit D

Figure 4:
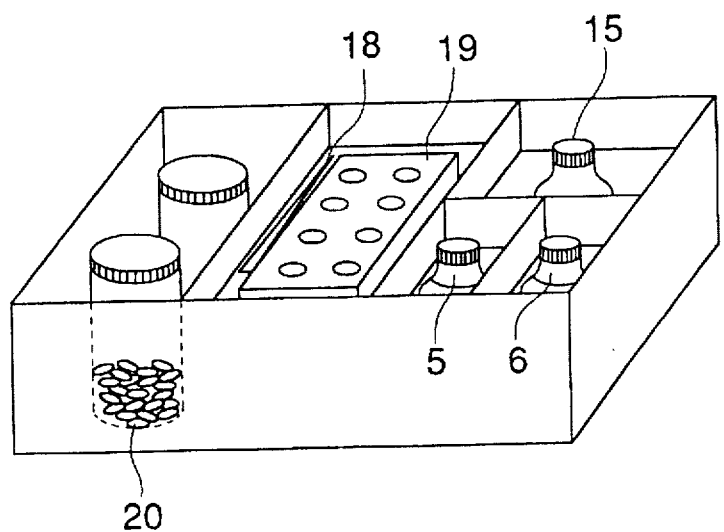
FIG. 4 is structural drawing of protein detection Kit D including a cotton-sphere-shaped sampling means, which is still another preferable embodiment of the present invention.

Structure of Kit D for detecting protein, which is still another embodiment of the present invention, cf. FIG. 4.

The Kit D is constituted by bottles 15 and 5 having the shape of an eye-drop-type bottle each filled with Reagent-A and Reagent-B, an eye drop bottle-shaped container 17 filled up with an isotonic sodium chloride solution 6, a sampling swab 20 composed of polyester fiber as a sampling means of the invention having a cotton sphere shape, a coloring reaction tray 19 and a pair of tweezers 18.

Other than the above-mentioned, a thermostat which can be adjusted at 60°, a spectroscopic photometer, a colorimeter, a standard color scale, if necessary, and a test tube stand are prepared.

Manner of handling Kit D

Put 1 ml of Reagent-A in the hollow place of the tray 19, and then add a few drops of Reagent-B, 5. Next, shake lightly the coloring reaction tray 19, to mix Reagents A and B. Pick the cotton sphere sampling swab 20 with the tweezers, and let it absorb a few drops the isotonic sodium chloride solution 6. Thus protein is transferred from a sample to the sampling swab 20 by wiping the sample surface in the similar manner described in the operational manner of the above-mentioned Kit A. Next, drop the cotton sphere in the hollow place of the coloring reaction tray 19. Stand the tray under the normal temperature or, if necessary, at 60° C. for one to 30 minutes, and cool it down in the room temperature. Semi-quantitative measurement of the protein absorbed in the sampling swab 1 is performed by comparing color with that of the standard scale.

2-5 Protein detection Kit E

Figure 5:
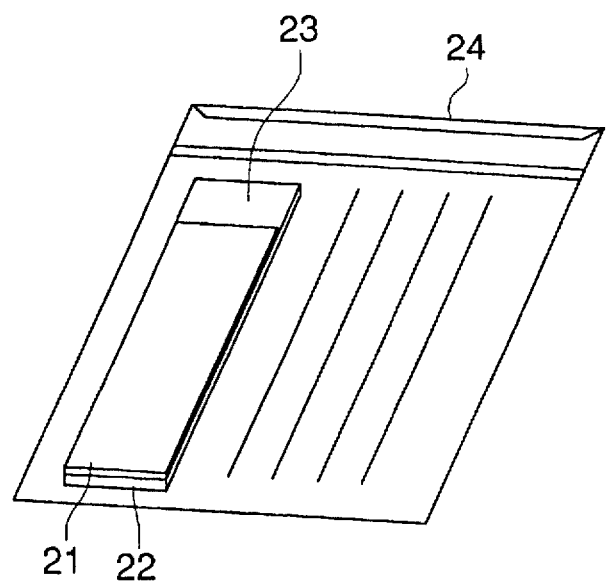
FIGS. 5a and 5b are structural drawings of protein detection Kit E including a strip-shaped sampling means, which is still another preferable embodiment of the present invention.
Figure 5:
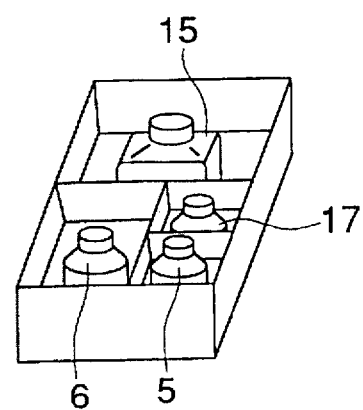

Structures Kit E for detecting protein, which is still another embodiment of the present invention (cf. FIG. 5).

Kit E is constructed by Reagent-A and reagent-B each filled in bottles 15 and 5 having the shape of an eye drop bottle, a bottle having an eye drop bottle-shape 17 for keeping Reagent-R, an eye drop bottle-shaped bottle filled up with an isotonic sodium chloride solution 6, a sampling means of the invention having a shape of film strip composed of a polystyrene film substrate 22 on which a filter paper like water absorbable layer composed of polyester fiber 21 is provided remaining a handle portion.

Other than the above-mentioned, a thermostatic which can be adjusted at 60° C., a colorimeter and, if necessary, a standard color scale are prepared.

Manner of handling Kit E

Add, 1 ml of Reagent-A and a few drops of Reagent-B into the reagent-R bottle 17, and lightly mix them for preparing reagent R. The reagent-R thus prepared is stably preserved for ten days under the normal temperature. Next, take a sampling strip from a case 24 with a zipper, and wet the water absorbable layer 21 by dropping it a few drops of the isotonic sodium chloride solution 6. Then, hold the hand holding portion 23, and bring the surface of the water absorbable layer 21 into contact with a sample and rub in the similar manner described in the operational manner of the above-mentioned Kit A. Then, set the sampling strip on a color forming reaction plate so as to contact the back surface of the substrate 22 to the plate and drop a few drops of reagent R from the bottle 17 on the surface of the water absorbable layer 21. Stand the strip either under the normal temperature or, if necessary, at 60° C. for one to 30 minutes, and cool down it in the room temperature. Thus, semi-quantitative measurement of the protein transferred on the sampling strip is performed by comparing color with that of the standard scale prepared beforehand.

2-6 Protein detection Kit F

Figure 6:
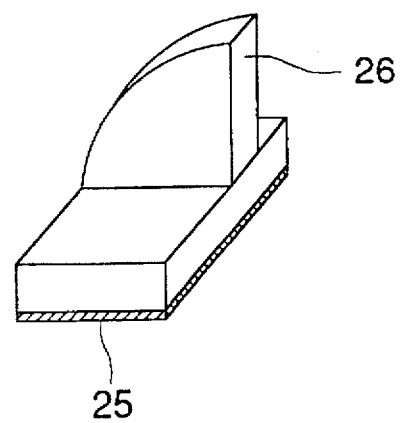
FIGS. 6a and 6b are structural drawing showing protein detection Kit F including a stamp-type sampling means, which is still another preferable embodiment of the present invention.
Figure 6:
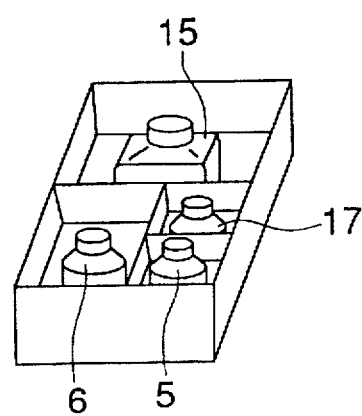

Structures and preparation of a kit for detecting protein, which is still another embodiment of the present invention, cf. FIG. 6

This kit is the same as Kit E except that the sampling filter 21 is attached to a step holder.

Manner of handling Kit F

Put 1 ml of Reagent-A and a few drops of Reagent-B into the bottle 17 and slightly mix them for preparing the Reagent-R. Reagent-R thus prepared can be stably preserved for ten days under the normal temperature. Take out the stamp holder 25, and wet the sapling filter by dropping a few drops of the isotonic sodium chloride solution. Then, hold the stamp holder 25, and contact and rub the surface of the sampling filter 26 with a sample in the similar manner described in the operational manner of the above-mentioned Kit A. Then, put a few drops of reagent-R on the surface of the filter and heat the holder under either the normal temperature or, if necessary, at 60° C. for one to 30 minutes, and cool down in the room temperature. Thus, semi-quantitative measurement of the protein absorbed in the sampling swab is performed by comparing color with that of the standard scale prepared beforehand.

3. Manner of coloring and sampling from a sample

Manner of coloring and that of sampling from the sample were compared. For investigation the standard measuring kit(2-1) was used.

<Sample>

First, an aqueous solution of BSA (bull serum albumin; 100 mg/ml) was put in a Petri dish, uniformly extended therein, and was dried in a dryer. For comparison, the similar procedure was carried out using an aqueous solution not containing BSA. These were provided as samples.

<Material used for the water absorbable portion of the detection swab>

Four kinds of detection swabs were prepared using the followings for as the materials of water absorbable portion thereof:

a. Polyester
b. Polyethylene
c. Natural cotton fiber for comparison

<Sampling of protein>

The surface of 10 cm square of the Petri dish with or without BSA coating is rubbed with the above-mentioned swab-stick sampling means. Respective sampling swabs were put in a tube as they were, and detection reaction was carried out in the foregoing procedure. For comparison, one without sampling swab was used. By measuring spectroscopic optical density at 562 nm of the liquid in the tube is measured by using a spectro-photometer. Results are shown in Table 1, in which comparison of the coloring density formed by the protein and the background coloring density are observed with respect to the three kind of the sampling means.

TABLE 1

| Material of swab | Sample with protein | Sample without protein (background coloring) |
| --- | --- | --- |
| a | 0.589 | 0.115 |
| b | 0.625 | 0.126 |
| c | 0.856 | 0.356 |
| Blank | 0.112 | 0.112 |

It is obviously understood that coloring level is low with respect to the sampling swabs in which synthetic fibers were used in comparison with that in which a natural cellulose was used.

Example 2

Effect of materials upon the reproduction performance of the result was investigated.

<Sampling swab>

As the material used for the water absorbable portion same materials as in Example 1 were used.

a. Polyester
b. Polyvinyl alcohol
c. Natural cotton fiber for comparison

<Sampling of Protein>

Fifty milliliter of a standard BAS solutions having a concentration of 1 mg/ml was absorbed slowly and completely in the water absorbable portion of the respective sampling swabs. Experiments were repeated for ten times with respect to the respective sampling swabs. Next, protein was detected by the use of Kit A. The measurement of the optical density at 562 nm of the liquid was carried out in the same manner as in Example-1. Average values of the color density and the variation coefficients of ten-time-measurement (n=10) of optical density are shown in Table-2.

TABLE 2

| Material of swab | Average Coloring density | Variation coefficient (n = 10) |
| --- | --- | --- |
| a | 0.855 | 8% |
| b | 0.842 | 9% |
| c | 1.128 | 18% |

It is understood that variation is small with respect to the sampling swab having the water absorbable portion made of a synthetic fiber in comparison with one in which a natural fiber is used.

Example 3

Background coloring caused sampling swab itself and its influence on the protein detection were investigated.

<Sampling swab>

The same materials as those used in Example-1 were used as the material for the water absorbable portion as follows:

a. polyester
b. polyvinyl alcohol and
c. natural cotton fiber for comparison

<Extraction of protein>

Detection reaction of the protein was carried out using the above-mentioned Kit C, and only reagent R was dropped to the respective sampling swabs. Background coloring was investigated by visual observation. The visual evaluation was made in five grades given below:

Color Evaluation

Green:—(color of non-reacted reagent)

Green with extremely pale purple: ±

Purple-green: + to +++ according to the increasing in the density of purple

Results are shown in Table-3.

TABLE 3

| material of saw | Coloring density |
|---|---|
| a | − |
| b | ± |
| c | ++ |

It is obviously understood that the background coloring caused by the sampling swab is lower when the synthetic fiber, especially polyester, is used in the water absorbable portion of the sampling means.

What is claimed is:

1. A method for detecting protein present on the surface of a sample comprising the steps of:

transferring a substance present on a subject portion of the surface of the sample to a sampling means which comprises a water absorbable portion comprising a water-insoluble synthetic polymer, contacting the substance transferred on the sampling means with a bicichoninic reagent which is capable of forming color upon reaction with protein, and detecting the presence of protein contained in the substance contacted with the reagent by color formation.

2. The method of claim 1, wherein said water absorbable portion of said sampling means is wetted with an aqueous liquid in advance to the transferring step.

3. The method of claim 1, wherein the step of contacting the reagent with the substance transferred to said sampling means is composed of the step of extracting the substance into an aqueous medium and the step of adding the reagent capable of forming color upon reaction with protein to said aqueous medium.

4. The method of claim 1, wherein the step of contacting said reagent with the substance transferred to said sampling means is composed the step of adding dropwise said reagent capable of forming color upon reaction with protein to the portion of the sampling means at which the substance are transferred from the surface of the sample.

5. The method of claim 1, wherein said water absorbable portion of said sampling means comprises a fibrous or porous water-insoluble sythetic polymer.

6. The method of claim 5, wherein said water absorbable portion of said sampling means comprises polyester fiber.

7. A kit for detecting protein including a combination of a sampling means comprising a water absorbable portion which comprises a water-insoluble synthetic polymer for transferring substance present on the subject portion of the surface of a sample and a bicichoninic reagent capable of forming color upon reaction with protein.

8. The kit of claim 7, wherein said water absorbable portion of said sampling means comprises polyester fiber.

9. The method of claim 1, wherein said method further comprises the step of measuring the degree of the color formation to determine the amount of protein contained in the substance contacted with the reagent.

* * * * *